United States Patent [19]

Sun et al.

[11] Patent Number: 5,672,340

[45] Date of Patent: Sep. 30, 1997

[54] ANTIPERSPIRANT DEODORANT COMPOSITIONS

[75] Inventors: Wei Mei Sun, Palatine; Zhu-ning Ma, Oak Park; Maximo M. Panitch, Skokie; Ramiro Galleguillos, Glendale Heights, all of Ill.

[73] Assignee: Helene Curtis, Inc., Chicago, Ill.

[21] Appl. No.: 612,771

[22] Filed: Mar. 7, 1996

Related U.S. Application Data

[63] Continuation of Ser. No. 199,499, Feb. 22, 1994, abandoned.

[51] Int. Cl.$^6$ .................................. A61K 7/38; A61K 7/34
[52] U.S. Cl. .................................. 424/66; 424/65; 424/68
[58] Field of Search .................................. 424/66, 68, 65

[56] References Cited

U.S. PATENT DOCUMENTS

| | | | |
|---|---|---|---|
| 2,607,658 | 8/1952 | Govett et al. | 23/14 |
| 2,645,616 | 7/1953 | Govett et al. | 252/317 |
| 2,876,163 | 3/1959 | Garizio et al. | 167/90 |
| 3,255,082 | 6/1966 | Barton | 167/90 |
| 4,268,499 | 5/1981 | Keil | 424/68 |
| 4,278,655 | 7/1981 | Elmi | 424/47 |
| 4,350,605 | 9/1982 | Hughett | 252/305 |
| 4,615,819 | 10/1986 | Leng | 252/110 |
| 4,673,570 | 6/1987 | Soldati | 424/66 |
| 4,725,430 | 2/1988 | Schamper et al. | 424/66 |
| 4,822,602 | 4/1989 | Sabatelli | 424/65 |
| 4,822,605 | 4/1989 | Powell | 424/85.2 |
| 4,948,678 | 8/1990 | Burger | 424/68 |

FOREIGN PATENT DOCUMENTS

| | | |
|---|---|---|
| 0 448 278 | 9/1991 | European Pat. Off. . |
| 0 450 597 | 10/1991 | European Pat. Off. . |
| 0 512 770 | 11/1992 | European Pat. Off. . |
| 0 550 960 | 7/1993 | European Pat. Off. . |
| WO 91/15191 | 10/1991 | WIPO . |
| WO 92/05767 | 4/1992 | WIPO . |
| WO 92/19222 | 11/1992 | WIPO . |

OTHER PUBLICATIONS

C. Fox, "Antiperspirants & Deodorants Review and Update", *Cosmetics & Toiletries*, 100 pp. 27–41 (1985).

Anon., "Deodorant & Antiperspriant Formula", *Cosmetics & Toiletries*, 100, pp. 65–75 (1985).

P.R. Howard et al. "Chapter 12–Systems Approach for Rheology Control", in *Polymers as Rheology Modifiers*, pp. 207–221 (1991).

R.L. Goldemberg et al. "Silicones in Clear Formulations" *D&CI*, Feb. 1986, pp. 33–44.

Remington's Pharmaceutical Sciences, 18th Ed. (1990), p. 761.

"The HLB System. A time saving guide to emulsifier selection". ICI Americas Inc. Wilemington, Delaware. Mar. 1980.

McCutcheon's Emulsitiers & Detergents. p. 28, vol. 1 1993.

Remingtons Pharmaceutical Sciences 18th Edition, 1990 p. 76.

*Primary Examiner*—C. Warren Ivy
*Assistant Examiner*—Evelyn Huang
*Attorney, Agent, or Firm*—Marshall, O'Toole, Gerstein, Murray & Borun

[57] ABSTRACT

Gelled or solid topically-effective compositions comprising a topically-active compound, like an antiperspirant compound; a borate crosslinker; a surfactant, and preferably, a nonionic surfactant or nonionic surfactant blend; a carrier comprising water; and, optionally, a hydrophobic compound, are disclosed.

30 Claims, No Drawings

ANTIPERSPIRANT DEODORANT COMPOSITIONS

This is a continuation of U.S. application Ser. No. 08/199,499, filed Feb. 22, 1994, now abandoned.

FIELD OF THE INVENTION

The present invention is directed to antiperspirant compositions comprising an antiperspirant compound, like an astringent salt; a borate crosslinker, like boric acid; a surfactant, preferably a nonionic surfactant or, more preferably, a nonionic surfactant blend, having an HLB value of about 3 to about 20; a carrier; and optionally, a hydrophobic compound, like a siloxane. The antiperspirant compositions are gelled or solid compositions that typically are transparent, phase stable and essentially nonwhitening and nonstaining to skin and clothing after topical application; effectively deliver the antiperspirant compound to the skin; and exhibit excellent sensory properties. The present invention also is directed to methods of using the antiperspirant compositions, and to gelled or solid topically-effective compositions in general.

BACKGROUND OF THE INVENTION

Antiperspirant compositions are well-known in the cosmetic art. An ideal antiperspirant composition is stable for the life of the composition, effectively delivers the antiperspirant compound to the skin, does not leave a visually-observable white residue on the skin or clothing, and is esthetically pleasing to the consumer.

Antiperspirant compositions are available in a variety of forms, such as aerosol suspensions; pump sprays; roll-on powders; emulsions or suspensions; and solid gels, waxes or suspensions. Antiperspirant compositions traditionally have been prepared as either oil-in-water emulsions or water-in-oil emulsions. Therefore, antiperspirant compositions of any form typically have a milky or opaque appearance and are manufactured by complex methods. Antiperspirant compositions prepared as emulsions often feel wet or oily when applied to the skin, and often remain tacky after the carrier of the composition evaporates. In addition, many emulsion-type antiperspirant compositions leave a white, staining residue on contacted skin or clothing.

Gelled emulsion-type antiperspirant compositions are used by rubbing an area of the body, such as the underarm, to apply a layer of the composition to the skin, and thereby reduce odor and/or perspiration. Gelled or solid antiperspirant compositions preferably possess the esthetic properties of nonbrittleness, smoothness, nonoiliness and nontackiness. Clarity, or transparency, of antiperspirant compositions also is a long-sought desirable esthetic property. Another highly desirable, but hard to achieve, esthetic property is avoiding a visible residue, e.g., a white layer, that is left on the skin or clothing after the antiperspirant composition is applied.

Nonemulsified antiperspirant compositions also are known in the art. However, nonemulsified compositions often require shaking prior to each use in order to redisperse the insoluble antiperspirant compound that has separated from the composition. Nonemulsified antiperspirant compositions that do not require shaking prior to each use, such as an antiperspirant creme or paste, typically include a relatively high percentage of suspending agents, like an organoclay. The presence of an organoclay in an antiperspirant composition is a principal source of the whitening and staining of skin and clothing.

Investigators have searched for antiperspirant compositions, and especially transparent antiperspirant compositions, that display the above-listed desirable properties. A gelled or solid antiperspirant composition is difficult to formulate and manufacture because the composition requires sufficient firmness to withstand rubbing across the skin to deliver a sufficient amount of the antiperspirant compound to the skin, and the composition also should be nonbrittle to resist fracturing and crumbling. Additional formulation parameters include viscosity control, lack of syneresis and nontackiness. Transparent, gelled or solid antiperspirant compositions are more difficult to formulate because of the added requirement of transparency.

A transparent gelled or solid antiperspirant composition which has esthetic and functional properties equal to or better than presently-available antiperspirants compositions is highly desired by consumers. However, providing a commercially-acceptable, transparent gelled or solid antiperspirant composition requires overcoming several formulation and manufacturing problems.

Transparent antiperspirant compositions, especially in the gel or solid, i.e., stick, form, are particularly favored by consumers because such transparent products are esthetically-appealing and project the appearance of product purity, safety, good performance and being non-whitening. However, due to the instability and the difficult manufacture of transparent compositions, transparent antiperspirant compositions are not readily available to consumers.

Solid antiperspirant compositions are divided into three main classes, i.e., compressed powder sticks, gel sticks and wax sticks. Each of these classes has advantages, but each class also has particular disadvantages. Compressed powder sticks for example are frequently brittle and hard, and leave a cosmetically-unacceptable powdery residue after application. Frequently, wax-based products are cosmetically unacceptable because of such factors as hardness, greasiness and tackiness. The opacity of wax sticks and the visually-observable white residue remaining after application also are esthetically undesirable.

Gel-type solid antiperspirant compositions have several advantages over both compressed powder sticks and wax sticks. For example, the gelled antiperspirant compositions leave less residue or dust on the skin. The gelled antiperspirant compositions also glide easily over the skin surface resulting in an easy and comfortable application of the composition.

However, the preparation of antiperspirant compositions in the form of an effective and stable gel is difficult. For example, a critical ingredient in gelled antiperspirant compositions is the gelling agent. Many prior gelled antiperspirant compositions comprise gelled hydroalcoholic solutions including a gelling agent, such as sodium stearate, to form the gel. However, common gelling agents cannot be used in the presence of acidic antiperspirant compounds because of an interaction between the gelling agent, which is alkaline, and the antiperspirant compound.

Prior transparent, gelled or solid antiperspirant compositions also typically were divided into three main classes. One of these classes is the optically-clear gelled emulsion compositions. These compositions include a water phase and an oil phase. The oil phase is suspended in the water phase by using a sufficient amount of an appropriate emulsifier or emulsifiers. The emulsions conventionally contained waxes, silicones, clays and emollients. The optically-clear gelled emulsion compositions are illustrated in U.S. Pat. Nos. 4,673,570, 4,268,499, 4,278,655, and 4,350,605;

EP 0 450 597; and in "Deodorant and Antiperspirant Formulary", *Cosmetics & Toiletries*, Dec. 12, 1985, vol. 100, p. 65–75.

The optically-clear gelled emulsion compositions often exhibit the disadvantages of composition instability during storage; the development of a hazy or milky appearance during storage; a stringy, tacky, oily consistency and other undesirable esthetics. In addition, the emulsion gel compositions often leave a visible residue, in the form of a white layer, on the skin or clothing. Another disadvantage of optically-clear gelled emulsion compositions is the complex method of preparing an optically-clear gelled emulsion composition. The method traditionally requires high shear rates during mixing, high processing temperatures, and a series of cooling and heating process steps. In one embodiment of the present invention, optically-clear gelled emulsion compositions are prepared by a simple method to provide antiperspirant compositions that overcome the above-described disadvantages of optically-clear gelled emulsion compositions.

A second class of transparent gelled or solid antiperspirant compositions is antiperspirant compositions thickened with 1,3:2,4-dibenzylidene-sorbitol (DBS) or DBS derivatives. Such transparent antiperspirant compositions are disclosed in U.S. Pat. Nos. 4,822,602 and 4,725,430; European Patent Publication 0 512 770; WO 91/15191; and WO 92/19222.

Transparent, gelled antiperspirant compositions thickened with DBS or DBS-type compounds have a major disadvantage in that the compositions are unstable in the presence of highly-acidic antiperspirant compounds at elevated temperatures. In addition, another disadvantage is the high temperature required for manufacturing DBS-thickened compositions (i.e., about 230° F. to about 240° F.).

The third class of transparent gelled or solid antiperspirant compositions is the acid-base complex gels. These transparent antiperspirant compositions are prepared by interacting the active antiperspirant compound with a carboxylic acid salt. Transparent acid-based complex gels are disclosed, for example, in U.S. Pat. Nos. 3,255,082 and 2,876,163; and in European Publication No. 0 448 278. Govett et al. U.S. Pat. Nos. 2,607,658 and 2,654,616 disclose a gel comprising an aluminum chlorohydroxy complex and a borate.

For example, EP 0 448 278 discloses complexing an antiperspirant aluminum salt with ammonium acetate. U.S. Pat. No. 2,876,163 discloses complexing an antiperspirant aluminum salt with various water-soluble inorganic salts, like an alkali metal oxide, hydroxide, or carbonate, or a salt of an organic or inorganic acid, such as sodium carbonate, sodium phosphate, or sodium glutamate.

This third class of transparent antiperspirant compositions has a major disadvantage in that the active antiperspirant compound is partially deactivated by the salt, thereby reducing the efficacy of the antiperspirant compound and, accordingly, the antiperspirant composition. In addition, the resulting gels or solids are very brittle, tacky, and/or possess other undesirable esthetic properties, such as in the compositions disclosed in U.S. Pat. No. 3,255,082, which are emulsions or sols and therefore are often opaque.

Although numerous patents disclose transparent gelled or solid antiperspirant compositions, the gelled compositions designated as clear or transparent do not have the clarity desired by consumers. Some transparent antiperspirant compositions also exhibit syneresis, or phase separation, during storage. Moreover, many of the prior art transparent compositions become cloudy or hazy after standing for a period of time. Typically, haziness increases to such an extent that the composition is cloudy and has little or no transparency about a month after preparation. Antiperspirant compositions conventionally have a product life in excess of one month. Therefore, the length of time the composition retains its transparency is an important esthetic property.

Investigators have continually sought to provide a gelled or solid antiperspirant composition having both long-term stability and sufficient esthetic and functional properties for consumer acceptance. These esthetic and functional properties include transparency, a sufficient hardness for application to the skin, a low degree of brittleness to resist fracture and crumbling of the composition, no visually-observable whitening of the skin and clothing, and the ability to effectively deliver the antiperspirant compound to the skin without providing a tacky or sticky feeling. The present invention is directed to providing gelled or solid antiperspirant compositions, and preferably transparent compositions, exhibiting these consumer-acceptable esthetic and functional properties.

SUMMARY OF THE INVENTION

The present invention relates to gelled or solid topically-effective compositions, and especially antiperspirant compositions, having improved efficacy and esthetics, and to methods of using the antiperspirant compositions. More particularly, the present invention is directed to a transparent, gelled or solid antiperspirant composition comprising an antiperspirant compound; a borate crosslinker; a surfactant, preferably a nonionic surfactant or a blend of nonionic surfactants, having an HLB value of about 3 to about 20; a carrier comprising water; and, optionally, a hydrophobic compound.

The "HLB value", or hydrophobic-lipophilic balance value, of a surfactant is a term well-known to those skilled in the art. The HLB value is related to the solubility of the surfactant, wherein a surfactant with a low HLB value, i.e., about 10 or less, tends to be oil-soluble and a surfactant with a high HLB value, i.e., greater than about 10, tends to be water-soluble.

In particular, the gelled or solid topically-effective compositions comprise:

(a) about 1% to about 40% by weight of an antiperspirant compound, like an astringent salt, or other water-soluble., topically-active compound;

(b) about 0.5% to about 10% by weight of a borate crosslinker, like boric acid, sodium tetraborate, or a mixture thereof;

(c) about 0.5% to about 70% by weight of a surfactant;

(d) a carrier comprising water; and (e) optionally, 0% to about 50% by weight of a hydrophobic compound, like a siloxane or a hydrocarbon. The transparent antiperspirant compositions are acidic in nature, having a pH of about 2 to about 6.

The transparent, gelled or solid antiperspirant compositions maintain composition clarity over extended storage periods, are essentially nonstaining and nonwhitening to skin and clothing, effectively deliver the antiperspirant compound to the skin, are nonbrittle, and exhibit excellent esthetic and functional properties, including sensory properties, for consumer acceptance. The present antiperspirant compositions remain transparent for at least six months when stored at room temperature.

In a preferred embodiment, the transparent gelled or solid antiperspirant composition comprises:

(a) about 5% to about 30% by weight of an aluminum or zirconium astringent salt, or a combination thereof;

(b) about 0.8% to about 7% by weight of a borate crosslinker;

(c) about 1% to about 50% by weight of a nonionic surfactant blend comprising a first nonionic surfactant having an HLB value of about 10 or greater and a second nonionic surfactant having an HLB value of less than about 10, wherein the nonionic surfactant blend has an HLB value of about 10 to about 15;

(d) a carrier comprising water; and (e) optionally, 0% to about 40% by weight of a hydrophobic compound, wherein the transparent antiperspirant composition has a pH of about 3 to about 5.

In another preferred embodiment, the transparent, gelled or solid antiperspirant compositions include a liquid crystal phase to provide a transparent antiperspirant composition when a hydrophobic compound is present in the composition.

The present invention also relates to methods of treating or preventing malodors associated with human perspiration, especially underarm odor. The methods comprise topically applying an effective amount of a gelled or solid antiperspirant composition of the present invention to the skin of a human.

The present invention also relates to transparent, gelled or solid compositions comprising a water-soluble topically-active compound, such as an analgesic, having improved sensory and esthetic properties. Such compositions further comprise a borate crosslinker, a nonionic surfactant or a nonionic surfactant blend, a carrier comprising water, and, optionally, a hydrophobic compound. The water-soluble topically-active compound is used in place of or in conjunction with the antiperspirant compound of the antiperspirant composition.

Therefore, in other embodiments of the present invention, the transparent, gelled or solid topically-effective composition incorporates water-soluble, topically-active drugs and medicaments; topical anesthetics; skin-soothing emollients and other topical cosmetic compounds; topical anti-inflammatories; and the like.

The above and other advantages and novel features of the present invention will become apparent from the following detailed description of the preferred embodiments of the invention.

DETAILED DESCRIPTION OF THE PREFERRED EMBODIMENTS

A gelled or solid antiperspirant composition of the present invention comprises an antiperspirant compound, a borate crosslinker, a nonionic surfactant or a nonionic surfactant blend, an aqueous-based carrier, and, optionally, a hydrophobic compound. In particular, the gelled or solid antiperspirant compositions have a pH of about 2 to about 6 and comprise:

(a) about 1% to about 40% by weight of an antiperspirant compound;

(b) about 0.5% to about 10% by weight of a borate crosslinker;

(c) about 0.5% to about 70% by weight of a surfactant;

(d) a carrier comprising water; and (e) optionally, 0% to about 50% by weight of a hydrophobic compound, such as a siloxane or a hydrocarbon. Typically, the antiperspirant compositions are transparent. As used here and hereinafter, the term "transparent" is defined as at least 50% transmittance determined spectrophotometrically at 700 nm (nanometers).

The following detailed description illustrates antiperspirant compounds. However, in addition to the antiperspirant compositions, a topically-effective composition including a water-soluble, topically-active compound other than or in addition to an antiperspirant compound, and ingredients (b) through (e) also demonstrate the improved sensory and esthetic properties of the antiperspirant compounds. Exemplary topically-active compounds include topically-effective drugs and medicaments, topical aesthetics, skin-soothing emollients and other topical cosmetic compounds, topical anti-inflammatories and the like. The present invention also relates to such topically-effective compositions.

The transparent gelled antiperspirant compositions are stable to phase separation, do not become hazy or milky during storage, and exhibit exceptional esthetic and functional properties. The antiperspirant compositions are nonbrittle, nonstringy and nontacky, and are capable of effectively delivering the antiperspirant compound to the skin, without leaving a visually-observable white residue on the skin or clothing, i.e., are essentially nonwhitening.

The present gelled antiperspirant compositions incorporate any of the antiperspirant compounds known in the art, such as the astringent salts. The astringent salts include organic and inorganic salts of aluminum, zirconium, zinc, and mixtures thereof. These astringent salts are polymeric in nature, and preferably contain hydroxyl moieties for interaction with a borate. The anion of the astringent salt can be, for example, sulfate, chloride, chlorohydroxide, alum, formate, lactate, benzyl sulfonate or phenyl sulfonate. Exemplary classes of antiperspirant astringent salts include aluminum halides, aluminum hydroxyhalides, zirconyl oxyhalides, zirconyl hydroxyhalides, and mixtures thereof.

Exemplary aluminum salts include aluminum chloride and the aluminum hydroxyhalides having the general formula $Al_2(OH)_xQ_y \cdot XH_2O$, wherein Q is chlorine, bromine or iodine; x is about 2 to about 5; x+y is about 6, wherein x and y are not necessarily integers; and X is about 1 to about 6. Exemplary zirconium compounds include zirconium oxy salts and zirconium hydroxy salts, also referred to as zirconyl salts and zirconyl hydroxy salts, and represented by the general empirical formula $ZrO(OH)_{2-nz}L_z$, wherein z varies from about 0.9 to about 2 and is not necessarily an integer; n is the valence of L; 2-nz is greater than or equal to 0; and L is selected from the group consisting of halides, nitrate, sulfamate, sulfate, and mixtures thereof.

The antiperspirant compound is present in the gelled antiperspirant composition in an amount of about 1% to about 40%, and preferably about 5% to about 30%, by weight of the composition. To achieve the full advantage of the present invention, the antiperspirant compound is present in an amount of about 10% to about 25% by weight of the antiperspirant composition.

The antiperspirant compounds are water-soluble. Exemplary antiperspirant compounds therefore include, but are not limited to, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof. Numerous other useful antiperspirant compounds are listed in WO 91/19222 and in the CTFA *Cosmetic Ingredient Handbook*, The Cosmetic, Toiletry and Fragrance Association, Inc., Washington, DC, p. 56, 1988, hereinafter the *CTFA Handbook*, incorporated herein by reference.

Preferred antiperspirant compounds are the aluminum-zirconium chlorides complexed with an amino acid, like glycine, and the aluminum chlorohydrates. Preferred aluminum-zirconium chloride glycine complexes have an aluminum (Al) to zirconium (Zr) ratio of about 1.67 to about 12.5, and a total metal (Al+Zr) to chlorine ratio (metal to chlorine) of about 0.73 to about 1.93. These antiperspirant compounds typically are acidic in nature, thereby providing a gelled antiperspirant composition having a pH less than 7, and typically having a pH of about 2 to about 6, and preferably about 3 to about 5.

In accordance with another important feature of the present invention, a wide variety of water-soluble, topically-active compounds can be incorporated into a transparent, gelled or solid composition of the present invention. The water-soluble, topically-active compounds can be incorporated into the present compositions in an amount of about 1% to about 40%, and preferably about 5% to about 30%, by weight of the composition. Such topically-active compositions include both cosmetic and medicinal compounds that act upon contact with the skin or hair. The resulting topically-effective compositions demonstrate essentially no phase separation if the topically-active compound is solubilized in the composition.

The topically-active compound can be a cosmetically-active compound, a medically-active compound or any other compound that is useful upon application to the skin or hair. Such topically-active compounds, in addition to antiperspirants, include antidandruff agents, antibacterial compounds, antifungal compounds, anti-inflammatory compounds, topical anesthetics and other cosmetic and medical topically-active compounds.

Therefore, in accordance with an important feature of the present invention, the transparent, gelled or solid topically-effective composition can include any of the above-described antiperspirant compounds. In addition to antiperspirant compounds, other topically-active compounds can be included in the transparent compositions of the present invention in an amount sufficient to perform their intended function. For example, water-soluble topically-active drugs, like antifungal compounds; antibacterial compounds; anti-inflammatory compounds; topical anesthetics; skin rash, skin disease and dermatitis medications; and anti-itch and irritation-reducing compounds can be included in the compositions of the present invention.

For example, analgesics, such as benzocaine, dyclonine hydrochloride and the like; anesthetics such as butamben picrate, lidocaine hydrochloride, xylocaine and the like; antibacterials and antiseptics, such as povidone-iodine, polymyxin b sulfate-bacitracin, zinc-neomycin sulfate-hydrocortisone, methylbenzethonium chloride, and erythromycin and the like; antiparasitics; deodorants, such as chlorophyllin copper complex and methylbenzethonium chloride; dermatologials, like ache preparations, such as benzoyl peroxide, erythromycin-benzoyl peroxide, clindamycin phosphate and the like; anti-inflammatory agents, such as alclometasone dipropionate, betamethasone valerate, and the like; burn relief ointments; depigmenting agents; dermatitis relief agents, such as the active steroid amcinonide, diflorasone diacetate, hydrocortisone, and the like; diaper rash relief agents, such as methylbenzethonium chloride and the like; fungicides; herpes treatment drugs; pruritic medications; and psoriasis, seborrhea and scabicide agents. Any other medication capable of topical administration also can be incorporated in a transparent composition of the present invention in an amount sufficient to perform its intended function.

In addition to the antiperspirant compound, a antiperspirant composition exemplifying the present invention also incorporates a borate crosslinker, like boric acid or sodium tetraborate. Exemplary borate crosslinkers include, but are not limited to, boric acid, sodium borate, borax (sodium tetraborate), sodium metaborate, boron oxide ($B_2O_3$), oligomers of boric acid, potassium pentaborate, potassium metaborate, sodium triborate, metaboric acid ($HBO_2$), ammonium hydrogen tetraborate, magnesium borate, barium metaborate, calcium metaborate, orthoboric acid, lithium metaborate, lithium tetraborate, zirconium metaborate, and mixtures thereof. The borate acts as a crosslinking agent to provide transparent antiperspirant compositions having sufficient structural integrity to perform as a gelled or stick deodorant. To achieve the full advantage of the present invention, the borate crosslinker is boric acid or sodium tetraborate.

The borate crosslinker is present in a gelled or solid antiperspirant composition in an amount of about 0.5% to about 10%, and preferably, about 0.8% to about 7%, by weight of the composition. To achieve the full advantage of the present invention, the gelled or solid antiperspirant composition includes about 2% to about 6%, by weight of the composition, of a borate crosslinker. As will be demonstrated in more detail hereinafter, as the amount of borate crosslinker in the antiperspirant composition is increased relative to a particular amount of antiperspirant compound, the antiperspirant composition increases in firmness and brittleness. Therefore, a person skilled in the art can select an amount of borate crosslinker relative to a particular amount of antiperspirant compound to provide a gelled antiperspirant composition through a solid antiperspirant composition of desired firmness and brittleness. The antiperspirant composition preferably is transparent.

It is theorized, but not relied upon herein, that the borate crosslinker interacts with and crosslinks the antiperspirant compound, e.g., an aluminum chlorohydrate. Accordingly, the antiperspirant compound, which is oligomeric or polymeric in nature, is crosslinked by the borate crosslinker to thicken and gel the antiperspirant composition to form a transparent, gelled or solid antiperspirant composition. In particular, it is theorized, but not relied upon herein, that the crosslinking occurs through interaction of the hydroxyl groups of the antiperspirant compound with the borate ion to produce bridges. Consequently, the borate bridges introduce a sufficient number of crosslinking sites that provide either gelled transparent semisolid compositions or transparent solid antiperspirant compositions. Because the antiperspirant compound is acidic, the crosslinking reaction occurs under acidic conditions (i.e., pH of about 2 to about 6).

The borate crosslinking agent is essential to providing a gelled or solid antiperspirant composition. As used here and hereinafter, the term "gel" is defined as a nonflowable composition that retains its shape in the free form (i.e., is unsupported) at room temperature (i.e., about 25° C.) for at least one day.

Other polybasic inorganic acids and salts were tested for an ability to crosslink with the antiperspirant compound. The following Examples 1 through 9 illustrate that various polybasic inorganic acids and salts are not capable of crosslinking the antiperspirant compound, whereas Examples 10-13 illustrate that a borate crosslinking agent can crosslink the antiperspirant compound. In each composition of Examples 1-9, no gel or solid formation was observed after standing for a period of two hours to two days. In Examples 2, 3, 4, 8 and 9, a white precipitate formed when the polybasic inorganic acid or salt was added to the composition.

the surfactant or the surfactant blend also affects the hardness of the antiperspirant composition.

A gelled or solid antiperspirant composition including an antiperspirant compound, like an aluminum chlorohydrate, and a borate crosslinker, like boric acid, is a transparent, hard and brittle composition. The firmness and brittleness can be adjusted to provide a commercially acceptable product. However, surprisingly, by incorporating a sufficient amount of a surfactant, and preferably nonionic surfactant or nonionic surfactant blend, the antiperspirant composition

| Ingredients | Example 1[1] | Example 2 | Example 3 | Example 4 | Example 5 | Example 6 | Example 7 | Example 8 | Example 9 |
|---|---|---|---|---|---|---|---|---|---|
| Antiperspirant Compound | 25[2] | 25 | 22 | 22 | 22 | 22 | 22 | 22 | 22 |
| Propylene Glycol | 45 | 45 | 40 | 40 | 40 | — | — | 40 | — |
| Water | 25 | 25 | 33.4 | 35.7 | 33.4 | 73.4 | 68 | 33.4 | 73.4 |
| Polybasic Inorganic Acid | 5[3] | 5[4] | 4.6[5] | 2.3[5] | 4.6[6] | 4.6[6] | 10.0[6] | 4.6[7] | 4.6[7] |
| pH | 3.7 | 4.35 | 5.7 | 5.7 | 3.1 | 3.5 | 3.2 | 3.3 | 3.1 |
| Appearance | Clear, fluid solution | White precipitate, dark green solution | White precipitate, solution | White precipitate solution | Clear, fluid solution | Clear, fluid solution | Clear, fluid solution | White precipitate, solution | White precipitate, solution |

[1] the amount of each ingredient is expressed as % by weight of the total composition, all percents set forth the amount of each ingredient actually present in the composition;
[2] aluminum chlorohydrate (ACH), available commercially as CHLOROHYDROL, from Reheis, Inc., Berkeley Heights, New Jersey, added as a 50% weight percent solution of ACH in water;
[3] sodium metatungstenate;
[4] sodium metavanadate;
[5] trisodium phosphate;
[6] phosphoric acid; and
[7] silicic acid.

In contrast, a composition including only sufficient amounts of an antiperspirant compound, a borate crosslinker and an aqueous carrier is a transparent gel or solid. When too low an amount of borate crosslinking agent is used, transparent gels are not sufficiently firm to serve as a solid antiperspirant compound. However, when too high an amount of borate crosslinking agent is used, the solid compositions are too brittle for commercial use. Such brittle antiperspirant compositions easily fracture or crumble during use making such transparent solid antiperspirants commercially unacceptable.

Therefore, in addition to the antiperspirant compound and the borate crosslinker, a gelled or solid antiperspirant composition of the present invention also includes about 0.5% to about 70%, and preferably about 1% to about 50%, by weight of the composition, of a surfactant, preferably a nonionic surfactant or a nonionic surfactant blend, having an HLB value of about 3 to about 20. More preferably, the surfactant is present in an amount of about 2% to about 30%, by weight of the composition. To achieve the full advantage of the present invention, an antiperspirant composition includes a nonionic surfactant having an HLB of about 10 to about 15, or a nonionic surfactant blend comprising a first nonionic surfactant having an HLB value of about 10 or greater and a second nonionic surfactant having an HLB of less than about 10, wherein the nonionic surfactant blend has an HLB of about 10 to about 15.

The surfactant also tolerates a pH of about 2 to about 6, and resists precipitation from solution in the presence of a relatively high salt concentration. The surfactant or surfactant blend preferably is present in a sufficient amount to form a liquid crystal phase. The surfactant or surfactant blend acts as a viscosity modifier or thickener, reduces the brittleness of solid antiperspirant compositions and does not contribute to whitening of skin or clothing. The amount and identity of remains transparent and firm, but the brittleness of the composition is reduced significantly. Accordingly, a transparent, gelled or solid antiperspirant composition of the present invention retains its structural integrity, is resistant to fracture and crumbling, and therefore is commercially acceptable.

A preferred surfactant is a nonionic surfactant or surfactant blend having an HLB value of about 3 to about 20. More preferred nonionic surfactants or nonionic surfactant blends have an HLB value of about 10 to about 15 and tend to be hydrophilic, and therefore soluble or dispersible in polar liquids, like water, alcohols and glycols. As will be described in more detail hereinafter, water and such polar liquids are carriers of the antiperspirant compositions of the present invention. The nonionic surfactant or surfactant blend also is soluble in, and does not precipitate from, a polar liquid in the presence of a relatively high salt concentration and at a pH of about 2 to about 6.

A nonionic surfactant having an HLB value of about 3 to about 20, and preferably about 10 to about 15, can be used alone as the nonionic surfactant of the present invention. Nonionic surfactants having an HLB value of at least about 10 also can be used as the first surfactant of a nonionic surfactant blend having an HLB value of about 10 to about 15. Typically, nonionic surfactants having an HLB value of at least about 10 have a hydrophobic base, such as a long chain alkyl group or an alkylated aryl group, and a hydrophilic chain comprising a sufficient number of ethoxy and/or propoxy moieties.

A nonionic surfactant having an HLB of less than about 10 is the second nonionic surfactant of the nonionic surfactant blend having an HLB of about 10 to about 15. The nonionic surfactants having an HLB of less than about 10 typically have the same type hydrophobic base as the high HLB surfactants, but include fewer ethoxy and/or propoxy moieties.

The HLB value of a particular nonionic surfactant can be found in *McCutcheon's Emulsifiers and Detergents, North American and International Editions*, MC Publishing Co., Glen Rock, N.J. (1993) (hereinafter *McCutcheon's*). Alternatively, the HLB value of a particular nonionic surfactant can be estimated by dividing the weight percent of oxyethylene in the surfactant by five (for surfactants including only ethoxy moieties). In addition, the HLB value of a nonionic surfactant blend can be determined by the following formula:

$$HLB = (wt. \% \ A) \ (HLB_A) + (wt. \% \ B) \ (HLB_B),$$

wherein wt. % A and wt. % B are the weight percent of nonionic surfactants A and B in the nonionic surfactant blend, and $HLB_A$ and $HLB_B$ are the HLB values for nonionic surfactants A and B respectively.

Exemplary classes of nonionic surfactants include, but are not limited to, polyoxyethylene ethers of fatty ($C_6$–$C_{22}$) alcohols, polyoxypropylene ethers of fatty ($C_6$–$C_{22}$) alcohols, dimethicone copolyols, ethoxylated alkylphenols, polyethylene glycol ethers of methyl glucose, polyethylene glycol ethers of sorbitol, and mixtures thereof.

Exemplary nonionic surfactants having an HLB value of 10 or greater that can be used alone or in the nonionic surfactant blend include, but are not limited to methyl gluceth-20, methyl gluceth-10, PEG-20 methyl glucose distearate, PEG-20 methyl glucose sesquistearate, PEG-200 castor oil, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-21 stearyl ether, polyoxyethylene-10 oleyl ether, polyoxyethylene-20 oleyl ether, an ethoxylated nonylphenol, ethoxylated octylphenol, ethoxylated dodecylphenol or ethoxylated fatty (C6–C22) alcohol including at least 9 ethylene oxide moieties, polyoxyethylene-20 isohexadecyl ether, dimethicone copolyol, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, and mixtures thereof.

Exemplary nonionic surfactants having an HLB value of less than 10 that can be used in the nonionic surfactant blend, include, but are not limited to, laureth-2, laureth-3, laureth-4, PEG-3 castor oil, an ethoxylated nonylphenol, ethoxylated octylphenol, ethoxylated dodecylphenol or ethoxylated fatty (C6–C22) alcohol having less than 9 ethylene oxide moieties, PEG 600 dioleate, PEG 400 dioleate, and mixtures thereof.

Numerous other nonionic surfactants having an HLB value of either about 10 or greater, or less than about 10 are disclosed in *McCutcheon's* at pages 1–246 and 266–272; in the *CTFA International Cosmetic Ingredient Dictionary, Fourth Ed.*, Cosmetic, Toiletry and Fragrance Association, Washington, DC (1991) (hereinafter the CTFA Dictionary) at pages 1–651; and in the *CTFA Handbook*, at pages 86–94, each incorporated herein by reference.

In addition to nonionic surfactants, anionic or cationic surfactants can be used as the surfactant. Exemplary anionic surfactants, such as salts of fatty ($C_8$–$C_{22}$) acids, are disclosed in *McCutcheon's* at pages 263–266, incorporated herein by reference. Exemplary cationic surfactants are disclosed in *McCutcheon's* at pages 272–273, incorporated herein by reference.

The carrier of the present gelled or solid antiperspirant composition comprises water. In addition, the carrier typically further comprises a water-soluble solvent. Exemplary carriers in addition to water include, but are not limited to, ethylene glycol, propylene glycol, butylene glycol, propylene carbonate, dimethyl isosorbide, hexylene glycol, ethanol, n-butyl alcohol, n-propyl alcohol, isopropyl alcohol, and mixtures thereof. The carrier is present in a sufficient amount to solubilize, disperse or hydrate the essential and optional ingredients of the transparent antiperspirant composition.

The transparent antiperspirant composition also can include a water-insoluble, or hydrophobic, compound, such as isohexadecene or 1-decene dimer. Such water-insoluble compounds are not present as a carrier of the composition, but are included as optional ingredients for a specific purpose, such as faster drying time, better skin feel, or ease of application. The hydrophobic compound either is emulsified by the nonionic surfactant, or preferably, is solubilized by the hydrophobic base of the nonionic surfactant in a liquid crystal phase.

The hydrophobic compound can be, for example, an aliphatic hydrocarbon, an water-insoluble ester, an water-insoluble ether, a fatty ($C_8$–$C_{12}$) alcohol or a siloxane. These hydrophobic compounds improve the feel of the antiperspirant composition on the skin, allow easier application of the antiperspirant composition to the skin, and allow the skin to dry faster after application of the antiperspirant composition.

Hydrophobic aliphatic hydrocarbons incorporated into the transparent antiperspirant composition include, for example, hydrogenated polybutenes, isoeicosane, isohexadecane, 1-decene dimer, mineral oils, nonvolatile hydrocarbon fluids, and hydrocarbons depicted in general structural formula (I), wherein n ranges from 2 to 5,

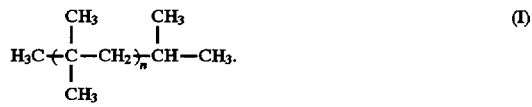

Volatile hydrocarbons, such as a hydrocarbon including about 10 to about 30 carbon atoms, have sufficient volatility to slowly volatilize from the skin after application of the antiperspirant composition. The volatile hydrocarbons provide benefits such as lubrication, a rich feel during application and faster drying. Specific volatile hydrocarbons having the structural formula (I) are the commercially-available compounds PERMETHYL 99A and PERMETHYL 101A, corresponding to compounds of general structure (I) wherein n is 2 and 3, respectively, and PERMETHYL 102A, available from Permethyl Corporation, Pottstown, Pa.

Siloxanes included in the transparent antiperspirant compositions provide the same benefits as the aliphatic hydrocarbons. Exemplary siloxanes include phenyltrimethicone; cyclic or linear, low molecular weight, volatile polydimethylsiloxanes known as cyclomethicones and dimethicones, respectively; and methicones. The cyclomethicones are low viscosity, low molecular weight, water-insoluble cyclic compounds having an average of about 3 to about 6—[O-Si(CH$_3$)$_2$]— repeating group units per molecule. Cyclomethicones are available commercially under the tradenames SILICONE 344 FLUID and SILICONE 345 FLUID from Dow Corning Corporation, Midland, Mich., and SILICONE SF-1173 and SILICONE 8F-1202 from General Electric, Waterford, N.Y., for example.

An example of a linear, low molecular weight, volatile dimethicone is the compound hexamethyldisiloxane, available commercially under the tradename DOW CORNING 200 FLUID, from Dow Corning Corp., Midland, Mich. DOW CORNING 200 FLUID has a viscosity of 0.65 cs (centistokes), is highly volatile, is non-greasy, provides lubrication for topical application of the composition of the present invention to the skin. Other linear polydimethylsiloxanes, such as decamethyltetrasiloxane, octamethyltrisiloxane, and dodecamethylpentasiloxane, also have sufficient volatility to provide a dry feel after application. Other useful linear siloxanes are hexyl dimethicone, polyphenylmethylsiloxane and bisphenylhexamethicone. Nonvolatile siloxanes also can be used as the hydrophobic compound. The volatile siloxanes and aliphatic hydrocarbons can be used alone, in combination, or in combination with nonvolatile siloxanes and/or nonvolatile aliphatic hydrocarbons.

Other suitable hydrophobic compounds include waxes, oils and fats, and water-insoluble emollients, like fatty ($C_8$–$C_{22}$) alcohols, ethers and esters. Exemplary hydrophobic compounds include, but are not limited to, dioctyl adipate, isopropyl myristate, isopropyl palmitate, isostearyl benzoate, and polypropylene-15 stearyl ether. Typical emollients are listed in the CTFA Handbook at page 23 through 28, incorporated herein by reference.

In addition to the essential ingredients and the optional softening agent, the present gelled or solid antiperspirant compositions also can include other optional ingredients traditionally included in antiperspirant compositions. These optional ingredients include, but are not limited to, dyes, fragrances, preservatives, antioxidants, detackifying agents, deodorizing agents, and similar types of compounds. These optional ingredients typically are included in the antiperspirant composition in an amount of about 0.01% to about 10% by weight of the composition.

The present gelled or solid antiperspirant compositions typically are transparent. However, opacifying agents, pearlescent agents or fillers (e.g., titanium dioxide or a styreneacrylamide latex) that render the antiperspirant composition nontransparent also can be included in the composition. The presence of such ingredients does not adversely effect the efficacy of the composition and are added to achieve a desired esthetic effect. Preferably, however, the antiperspirant composition is transparent, and typically is transparent unless rendered opaque by an intentionally-added optional ingredient.

To demonstrate the gelled or solid antiperspirant compositions of the present invention, the following nonlimiting examples were prepared. In some cases, the composition of a particular example was compared to other examples for an esthetic or functional property. As will be demonstrated in the following examples, an antiperspirant composition of the present invention leaves essentially no white residue, i.e., leaves no visually-observable white residue. Such a result is surprising because a white residue, attributable to the solid antiperspirant compound, typically is observed after other antiperspirant composition ingredients evaporate. In addition to being nonwhitening, the present antiperspirant compositions have the added esthetic benefit of being transparent. Heretofore, transparency has been difficult to achieve in gelled or solid antiperspirant compositions because the gelling agents either interacted with the antiperspirant compound or were ineffective at a low pH of about 2 to about 6.

In accordance with another important feature of the present invention, the transparent gelled or solid antiperspirant compositions of the present invention are manufactured by simply admixing composition ingredients at a relatively low temperature. Contrary to prior methods of manufacturing gelled or solid antiperspirant compositions, the elevated temperatures needed to melt the gelling agents, and the long cooling times to provide the antiperspirant composition, are not required.

In one embodiment, an antiperspirant composition of the present invention is prepared by forming an aqueous solution of the antiperspirant compound and the borate crosslinker in the aqueous-based carrier. This aqueous solution then is admixed with the nonionic surfactant or nonionic surfactant blend and, if present, the hydrophobic compound, to provide a transparent solid or gelled antiperspirant composition. The borate crosslinker also can be added at a later time or in conjunction with the hydrophobic compound.

Preferably, the antiperspirant compositions are prepared by forming a liquid crystal phase prior to the addition of the borate crosslinker. A surfactant liquid crystal phase is formed by the nonionic surfactant or nonionic surfactant blend in the presence of the antiperspirant compound, carrier and optional hydrophobic compound. This combination of ingredients forms a viscous liquid to soft gel. Next, the borate crosslinker is added to the composition, and agitation is maintained until the mixture is homogeneous.

The combination of liquid crystals and borate crosslinker provides a gelled to solid composition having a consistency and firmness suitable for an antiperspirant composition. The firmness of the antiperspirant composition is controlled by a judicious selection of the amount of borate crosslinker incorporated into the composition.

The formation of a liquid crystal phase provides the advantages of incorporating the hydrophobic compound into the composition and providing a transparent antiperspirant composition. In addition, less borate crosslinker is incorporated into the composition to achieve a predetermined composition consistency and firmness.

The amount of borate crosslinker included in the antiperspirant composition therefore determines the time required for the antiperspirant compound to solidify, and determines the firmness and brittleness of the antiperspirant composition. The antiperspirant composition is transparent unless an intentionally-added optional ingredient provides an opaque or pearlescent composition.

As will be demonstrated in the following examples, the antiperspirant compositions were transparent and phase-stable over the life of the product; were firm and nonbrittle, thereby resisting cracking and crumbling; were easy to apply and effectively delivered the antiperspirant compound to the skin; and did not whiten the skin or clothing. Each of the following examples was prepared by the above-described method.

EXAMPLE 10

The compositions of Example 10–12 illustrate that a borate crosslinker incorporated into the antiperspirant composition, relative to the amount of antiperspirant compound, influences the physical form, texture, brittleness and solidification temperature, of the antiperspirant composition.

| Ingredients | Example 10[1)] |
| --- | --- |
| Antiperspirant Compound | 25.0[8)] |
| Propylene Glycol[9)] | 61.0 |
| Water[9)] | 7.5 |
| Borate Crosslinker[10)] | 6.0 |
| Fragrance | 0.5 |

[8)]aluminum zirconium glycinate (AZG) available commercially as REZAL 36GPG, from Reheis, Inc., Berkeley Heights, New Jersey, added as a 100% weight percent active material;
[9)]carrier; and
[10)]boric acid.

The composition of Example 10 illustrates that a transparent, fast-setting (about 30 minutes), solid antiperspirant composition can be manufactured. In the absence of a borate crosslinker the composition is a transparent, very viscous liquid. The viscosity of the composition increases with the amount of borate crosslinker. At a sufficiently high amount of borate crosslinker, in relation to the amount of antiperspirant compound, the composition solidifies.

However, the composition of Example 10 was brittle and susceptible to fracturing and crumbling. The composition of Example 10 also illustrated that a borate crosslinker crosslinks a different type of antiperspirant compound, i.e, AZG. The composition of Examples 10 exhibited long term stability at room temperature, and for at least one month at 50° C.

The compositions of Examples 11 and 12 illustrate that compositions including an antiperspirant compound and a borate crosslinker, but absent a nonionic surfactant or nonionic surfactant blend, are hard, brittle compositions. The compositions of Examples 11 and 12 took a longer time to solidify and were not as hard as the composition of Example 10. The decreased hardness and increased solidification time reflects the lower amount of borate crosslinker in Examples 11 and 12.

| Ingredients | Example 11[1] | Example 12 |
| --- | --- | --- |
| Antiperspirant Compound | 20.4[2] | 20.0[2] |
| Propylene Glycol[5] | 45.9 | 47.0 |
| Water[9] | 29.6 | 29.0 |
| Borate Crosslinker[10] | 4.1 | 4.0 |
| Properties: | Transparent; hard, brittle | Transparent; hard, brittle |

The compositions of Examples 11 and 12 each were transparent solid antiperspirant compositions, and were esthetically and functionally acceptable. The compositions of Examples 11 and 12 exhibited a decreased hardness and brittleness compared to the antiperspirant composition of Example 10. The hardness and brittleness of the compositions of Examples 10, 11 and 12 make the antiperspirant composition commercially acceptable to some, but not a majority of, consumers. The compositions of Examples 11 and 12 exhibited long term stability at room temperature, and for at least one month at 50° C.

| Example 13 (comparative) | |
| --- | --- |
| Ingredients[1] | |
| Aluminum Chlorohydrate[2] | 20 |
| Boric Acid[10] | 6 |
| Glycerin | 24 |
| Water[9] | 50 |

The comparative composition of Example 13 was a transparent, solid antiperspirant composition that does not incorporate a nonionic surfactant or nonionic surfactant blend. The comparative transparent composition of Example 13 was a brittle solid having a slightly rubbery consistency. Glycerin, which typically acts as a plasticizer, did not reduce the brittleness of the comparative composition of Example 13. The brittleness of the comparative composition of Example 13 made the antiperspirant composition commercially acceptable to some, but not to a majority of, consumers. Accordingly, it has been demonstrated that typical plasticizers, like polyols, do not reduce the hardness and brittleness of the antiperspirant compositions. A nonionic surfactant or nonionic surfactant blend therefore is used to provide a commercially-acceptable firm, but nonbrittle, gelled antiperspirant composition.

The following Examples 14–25 illustrate other embodiments of the present invention.

| | Example 14[1] | Example 15[1] |
| --- | --- | --- |
| Antiperspirant Compound | 23.2 | 25.25 |
| Nonionic Surfactant Blend | 18.4[11] | 24.1[13] |
| Water[9] | q.s. | q.s. |
| Boric Acid | 2.0 | 2.1 |
| Hydrophobic Compound | 25.0[12] | 22.1[14] |

[11] a blend of 11% by weight isoceteth-20 (HLB 15.7), available commercially from ICI Americas, Wilmington, DE as ARLASOLVE 200, as a 72% active solution, and 7.4% by weight laureth-4 available commercially from ICI Americas, Wilmington, DC, as BRIJ 30 (HLB 9.7), as a 100% active material;
[12] a blend of 12.5% by weight cyclomethicone, available commercially from Dow Corning Corporation as Silicone DC344, as a 100% active material, and 12.5% by weight isohexadecane, available commercially from Permethyl Corp., Pottstown, PA, as PERMETHYL 101A, as a 100% active material;
[13] a blend of 14.3% by weight ceteth-20 (HLB 15.7), available commercially from ICI Americas, Wilmington, DE, as BRIJ 58, as a 100% active material, and 9.8% BRIJ 30; and
[14] PERMETHYL 101A.

The compositions of Examples 14 and 15 were clear, hard solids. The compositions of Examples 14 and 15 incorporated a borate crosslinker and a nonionic surfactant blend in accordance with the present invention. The compositions of Examples 14 and 15 were prepared in a manner to provide liquid crystals. The compositions were stable compositions that applied to skin easily and did not leave a white residue on the skin after drying.

| | Example 16[1] | Example 17 |
| --- | --- | --- |
| Antiperspirant Compound | 24.4 | 23.0[17] |
| Nonionic Surfactant Blend | 24.9[15] | 21.6[18] |
| Water[9] | q.s. | q.s. |
| Boric Crosslinker[10] | 1.9 | 2.3 |
| Hydrophobic Compound | 20.6[16] | 22.7[19] |

[15] a blend of 16.5% by weight dimethicone copolyol, available from Goldschmidt Chemical Corp., Hopewell, VA, as ABIL B88184, as a 100% active material, and 8.4% by weight BRIJ 30;
[16] a blend of 10.1% by weight Silicone DC344 and 10.5% by weight isoeicosone, available commercially from Permethyl Corp., Pottstown, PA as PERMETHYL 120A, as a 100% active material;
[17] aluminum sesquichlorohydrate, added as a 46% active material;
[18] a blend of 11.2% by weight nonoxynol-40 (HLB 17.2), available commercially from Rhone-Poulenc Surfactants Div., Cranbury, NJ, as IGEPAL CO-890, as a 100% active material, and 10.4% by weight laureth-3, available as a 100% active material; and
[19] isopropyl myristate, available as a 100% active material.

The compositions of Examples 16 and 17 illustrate transparent gelled antiperspirant compositions of the present invention. The compositions of Examples 16 and 17 also illustrate that the nonionic surfactant effects the consistency of the composition. The composition of Examples 16 and 17 were firm and nonbrittle. Accordingly, a sufficient amount of nonionic surfactant or nonionic surfactant blend is present in the antiperspirant composition for a given amount of borate crosslinker to provide a firm, but nonbrittle composition.

In general, a sufficient amount of nonionic surfactant or nonionic surfactant blend is present in the antiperspirant composition if the composition has a penetrometer value in the range of about 4 to about 10 ram (millimeter). Below a penetrometer value of about 4 mm, the antiperspirant composition is too brittle and has a tendency to fracture and crumble. Above a penetrometer value of about 10 mm, the antiperspirant composition is too soft and has a tendency to flow. Preferably, the present antiperspirant compositions have a penetrometer value of about 5 to about 10 mm.

An important feature of the present invention is reduction of the white residue on skin and clothing resulting from the use of an antiperspirant composition. The absence of a white residue is a primary esthetic property desired by consumers in antiperspirant compositions.

Roll-on antiperspirants and present-day compressed powder stick antiperspirants leave a cosmetically-unacceptable white residue on the skin or clothing after application to the skin. The following Examples 18–21 demonstrate that incorporating a nonionic surfactant in gelled or solid antiperspirant compositions reduces brittleness and crumbling of the composition, and also reduces the white residue on skin and clothing.

| Ingredients | Example 18[1] | Example 19 | Example 20 | Example 21 |
|---|---|---|---|---|
| Antiperspirant Compound | 25.4[2] | 24.95[2] | 25.05[2] | 23.15[2] |
| Nonionic Surfactant | 21.4[20] | 22.3[22] | 21.4[23] | 24.7[25] |
| Borate Crosslinker | 1.8 | 2.5 | 1.9 | 2.5 |
| Hydrophobic Compound | 26.0[21] | — | 21.0[24] | 19.9[26] |
| Water | q.s. | q.s. | q.s. | q.s. |

[20]ARLASOLVE 200;
[21]PERMETHYL 101A;
[22]a blend of 8.3% by weight steareth-10 (HLB 12.4), available commercially from ICI Americas, Inc., Wilmington, DE, as BRIJ 76, as a 100% active material, and 14.0% by weight BRIJ 30;
[23]a blend of 13.9% PEG-20 glyceryl stearate (HLB 13.0), available commercially from Lonza, Inc., Fairlawn, NJ as ALDOSPERSE MS-20FG, as a 100% active material, and 7.5% by weight BRIJ 30;
[24]a blend of 10.5% by weight of cyclomethicone, available commercially as Silicone DC245 from Dow Corning Corp., Midland, MI as a 100% active material, and 10.5% PERMETHYL 102A;
[25]a blend of 20.0% POE(6)tridecylether (HLB 11.4), available commercially from PPG/Mazer, Gurnee, IL, as MACOL TD-6, as a 100% active material, and 4.7% by weight laureth-2; and
[26]a blend of 10.4% by weight Silicone DC-344 and 9.5% by weight mineral oil.

The compositions of Examples 18–21 were tested for whitening by individually applying 0.5 ml (milliliter) of each composition to a blackboard. Each composition was spread evenly on the blackboard with a doctor blade. The white residue left by each composition of Examples 18–21 and DEGREE was visually observed at 30 minutes and at 2 hours after application. The compositions of Examples 18–21 did not leave a visually observable white residue 30 minutes or 2 hours after application.

The following Examples 22–25 illustrate antiperspirant compositions of the present invention. The transparent, gelled or solid antiperspirant compositions were stable and effectively delivered the antiperspirant compound to the skin.

| Ingredients | % (by weight)[1] |
|---|---|
| Example 22 | |
| Aluminum Chlorohydrate[2] | 24.4 |
| Nonionic Surfactant | 23.6[26] |
| Borate Crosslinker[10] | 1.7 |
| Hydrophobic Compound | 21.5[27] |
| Water[9] | q.s. |

[26]a blend of 18.4% by weight PEG-80 castor oil (HLB 15.8), available from Chemax, Inc., Greenville, SC as CHEMAX-80, as a 100% active material and 5.2% by weight laureth-3;
[27]a blend of 11.0% by weight polyphenylmethylsiloxane, available commercially from Dow Corning, Inc., Midland, MI, as Silicone DC556, as a 100% active material, and 10.5% by weight of a synthetic isoparaffinic ($C_{13-14}$) hydrocarbon, available commercially from Exxon Chemical, Baytown, TX as ISOPAR M, as a 100% active material.

The composition of Example 22 was a transparent gelled solid having excellent esthetic and functional properties, including an excellent ability to deliver the antiperspirant compound. The composition of Example 22 did not leave a visually observable white residue on the skin.

| Ingredients | % (by weight)[1] |
|---|---|
| Example 23 | |
| Aluminum Chlorohydrate[2] | 24.35 |
| Borate Crosslinker[36] | 1.6 |
| Hydrophobic Compound | 21.7[29] |
| Nonionic Surfactant | 25.1[28] |
| Water[9] | q.s. |
| Example 24 | |
| Aluminum Chlorohydrate[2] | 23.6 |
| Borate Crosslinker[10] | 1.8 |
| Hydrophobic Compound | 26.3[31] |
| Nonionic Surfactant | 22.6[30] |
| Water[9] | q.s. |

[28]a blend of 13.6% by weight of steareth-21 (HLB 15.5), available commercially from ICI Americas, Inc., Wilmington, DE as BRIJ 721S, as a 100% active material, and 11.5% by weight BRIJ 30; and
[29]a blend of 16.3% by weight PERMETHYL 102A, 3.7% by weight PPG-15 stearyl ether, available from ICI Americas, Inc., Wilmington, DE as ARLAMOL E, as a 100% active material; and 1.7% by weight Silicone DC344 available commercially from Dow Corning Corporation, Midland, MI, as a 100% active material.
[30]a blend of 9.1% by weight of polysorbate 20 (HLB 16.7), available commercial from ICI Americas, Inc., Wilmington, DE as TWEEN 20, as a 100% active material, and 13.5% by weight BRIJ 30; and
[31]PERMETHYL 101A.

The compositions of Examples 23 and 24 were transparent solids having excellent phase stability, esthetic properties and functional properties. The compositions of Example 23 and 24 also were a transparent gelled antiperspirant composition having good esthetic properties.

In accordance with an important feature of the present invention, the transparent gelled antiperspirant compositions illustrated above incorporated a hydrophobic compound and maintained composition transparency, efficacy and esthetics. Such antiperspirant compositions therefore include a polar phase and an oil phase. The polar phase comprises the antiperspirant compound, water, other hydrophilic carriers, the borate crosslinker and any other water-soluble or water-dispersible optional ingredients. The oil phase includes the hydrophobic compound. The phases are joined by the nonionic surfactant or nonionic surfactant blend, preferably through the formation of a liquid crystal phase.

The following Examples 25–28 illustrate further embodiments of the present invention. The compositions of Examples 25–28 each were solid, transparent compositions having good esthetic properties and an excellent ability to deliver the antiperspirant compound to the skin. The compositions of Examples 25–28 include a nonionic surfactant or nonionic surfactant blend, and therefore, did not leave a visually-observable white residue on skin or clothing, were firm, were nonbrittle and resisted fracturing and crumbling.

| Ingredients | % (by weight)[1] |
|---|---|
| Example 25 | |
| Antiperspirant Compound[2] | 20.0 |
| Propylene Glycol[9] | 43.5 |
| Water[9] | 20.0 |
| Laureth-4[34] | 8.0 |
| Steareth-20[33] | 2.5 |
| $C_{12}$–$C_{15}$ Alkyl Benzoates | 0.5 |
| Cyclomethicone | 1.0 |
| Borate Crosslinker[10] | 4.0 |
| Fragrance | 0.5 |
| Example 26 | |
| Antiperspirant Compound[2] | 20.9 |
| Nonionic Surfactant | 24.9[35] |
| Hydrophobic Compound | 29.5[36] |
| Borate Crosslinker[10] | 1.9 |
| Water[9] | q.s. |
| Example 27 | |
| Antiperspirant Compound[2] | 20.25 |
| Nonionic Surfactant | 30.4[37] |
| Hydrophobic Compound | 29.0[38] |
| Borate Crosslinker[10] | 3.5 |
| Water[9] | q.s. |
| Example 28 | |
| Antiperspirant Compound[2] | 23.1 |
| Nonionic Surfactant | 21.0[39] |
| Hydrophobic Compound | 27.6[40] |
| Borate Crosslinker[10] | 4.5 |
| Water[9] | q.s. |

[32] SILICONE 344 FLUID, Dow Corning Corporation, Midland, MI;
[33] available as BRIJ 78 (HLB 15.3) from ICI Americas Corp., Wilmington, DE, as a 100% active material; and
[34] BRIJ 30.
[35] a blend of 12.7% by weight BRIJ 58, and 12.2% by weight DEG-8 dioleate (HLB 8.5), available commercially from PPG/Mazer, Gurnee, IL, as MAPEG 400 DE, as a 100% active material; and
[36] a blend of 16.0% by weight PERMETHYL 101A, and 13.5% by weight of a dimethicone fluid (350 centistokes), available commercially from Dow Corning Corp., Midland, MI, as DOW CORNING FLUID DC200 (350 cs), as a 100% active material.
[37] a blend of 15.2% by weight BRIJ 30, and 15.2% by weight ARLASOLVE 200L; and
[38] a blend of 9.3% by weight PERMETHYL 102A, and 19.7% Silicone DC344.
[39] a blend of 16.5% by weight BRIJ 30, and 10.5% by weight ARLASOLVE 200L; and
[40] a blend of 11.5% by weight Silicone DC344, 11.5% by weight PERMETHYL 102A, and 4.6% by weight MYVEROL 18-92 (formulated product including distilled monoglycerides with corn oil).

The transparent antiperspirant compositions of the present invention exhibit unique and superior properties upon topical application to skin. The improved physical and sensory properties include a firm, but nonbrittle, consistency to effectively deliver the antiperspirant compound to the skin; storage stability; elimination of the shaking requirement to redistribute the antiperspirant compound prior to use; essentially no whitening of the skin and clothing after topical application; and transparency for enhanced consumer acceptance.

It should be understood that the foregoing detailed description is given merely by way of illustration. Obviously, many modifications and variations of the invention as hereinbefore set forth can be made without departing from the spirit and scope thereof and therefore only such limitations should be imposed as are indicated by the appended claims.

What is claimed and desired to be secured by Letters Patent is:

1. A gelled or solid antiperspirant composition comprising:

(a) about 1% to about 40% by weight of an antiperspirant compound;

(b) about 0.5% to 10% by weight of a borate crosslinker;

(c) about 0.5% to about 70% by weight of a surfactant selected from the group consisting of a nonionic surfactant or a nonionic surfactant blend, wherein the nonionic surfactant and nonionic surfactant blend has an HLB value of about 3 to about 20; and (d) a carrier comprising water;

wherein the antiperspirant composition has a pH of about 3 to about 5, a penetrometer reading of about 4 mm to about 10 mm, and a % transmittance at 700 nm of at least 50%.

2. The composition of claim 1 wherein the nonionic surfactant or nonionic surfactant blend has an HLB value of about 10 to about 15.

3. The antiperspirant composition of claim 1 further comprising 0% to about 50% by weight of a hydrophobic compound selected from the group consisting of an aliphatic hydrocarbon, a fatty ($C_8$–$C_{22}$) alcohol, a siloxane, a water-insoluble ether, a water-insoluble ester, and mixtures thereof.

4. The antiperspirant composition of claim 1 wherein the composition is nonflowable and capable of maintaining a shape in the free form at room temperature for at least one day.

5. The antiperspirant composition of claim 1 wherein the antiperspirant compound is present in an amount of about 5% to about 30% by weight of the composition.

6. The antiperspirant composition of claim 1 wherein the antiperspirant compound is present in an amount of about 10% to about 25% by weight of the composition.

7. The antiperspirant composition of claim 1 wherein the antiperspirant compound is an astringent salt comprising aluminum, zirconium, zinc, or a mixture thereof.

8. The antiperspirant composition of claim 1 wherein the antiperspirant compound is selected from the group consisting of aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof.

9. The composition of claim 1 wherein the borate crosslinker is present in an amount of about 0.8% to about 7% by weight of the composition.

10. The composition of claim 1 wherein the borate crosslinker is present in an amount of about 2% to about 6% by weight of the composition.

11. The composition of claim 1 wherein the borate crosslinker is selected from the group consisting of boric acid, sodium borate, sodium tetraborate, sodium metaborate, boron oxide, an oligomer of boric acid, potassium pentaborate, potassium metaborate, sodium triborate, metaboric acid, ammonium hydrogen tetraborate, magnesium borate, barium metaborate, calcium metaborate, orthoboric acid, lithium metaborate, lithium tetraborate, zirconium metaborate, and mixtures thereof.

12. The composition of claim 1 wherein the surfactant is present in an amount of about 1% to about 50% by weight of the composition.

13. The composition of claim 1 wherein the surfactant is present in an amount of about 2% to about 30% by weight of the composition.

14. The composition of claim 2 wherein the nonionic surfactant blend comprises: (i) a first nonionic surfactant having an HLB value of about 10 or greater, and (ii) a second nonionic surfactant having an HLB of less than about 10, wherein a sufficient amount of the first nonionic surfactant is blended with a sufficient amount of the second nonionic surfactant to provide the nonionic surfactant blend having the HLB value of about 10 to about 15.

15. The composition of claim 2 wherein the nonionic surfactant is selected from the group consisting of a polyoxyethylene ethers of fatty ($C_6$–$C_{22}$) alcohol, a polyoxypropylene ethers of fatty ($C_6$–$C_{22}$) alcohol, a dimethicone copolyol, an ethoxylated alkylphenol, a polyethylene glycol ether of methyl glucose, a polyethylene glycol ether of sorbitol, and mixtures thereof.

16. The composition of claim 1 wherein the nonionic surfactant comprises methyl gluceth-20, methyl gluceth-10, PEG-20 methyl glucose distearate, PEG-20 methyl glucose sesquistearate, PEG-200 castor oil, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-21 stearyl ether, polyoxyethylene-10 oleyl ether, polyoxyethylene-20 oleyl ether, an ethoxylated nonylphenol having at least 9 ethylene oxide moieties, an ethoxylated octylphenol having at least 9 ethylene oxide moieties, an ethoxylated dodecyl phenol having at least 9 ethylene oxide moieties, an ethoxylated fatty ($C_6$–$C_{22}$) alcohol having at least 9 ethylene oxide moieties, polyoxyethylene-20 isohexadecyl ether, dimethicone copolyol, polyoxyethylene-23 glycerol laurate, polyoxyethylene-20 glyceryl stearate, PPG-10 methyl glucose ether, PPG-20 methyl glucose ether, a polyoxyethylene-20 sorbitan monoester, polyoxyethylene-80 castor oil, polyoxyethylene-15 tridecyl ether, polyoxyethylene-6 tridecyl ether, and mixtures thereof.

17. The composition of claim 16 further comprising laureth-2, laureth-3, laureth-4, PEG-3 castor oil, an ethoxylated nonylphenol, ethoxylated octyl phenol, ethoxylated dodecylphenol or ethoxylated fatty ($C_6$–$C_{22}$) alcohol having less than 9 ethylene oxide moieties, PEG 600 dioleate, PEG 400 dioleate, and mixtures thereof.

18. The composition of claim 1 wherein the carrier further comprises ethylene glycol, propylene glycol, butylene glycol, propylene carbonate, dimethyl isosorbide, hexylene glycol, ethanol, n-butyl alcohol, n-propyl alcohol, isopropyl alcohol, and mixtures thereof.

19. The antiperspirant composition of claim 3 wherein the hydrophobic compound is an aliphatic hydrocarbon selected from the group consisting of a hydrogenated polybutene, isoeicosane, isohexadecane, 1-decene dimer, a mineral oil, a nonvolatile hydrocarbon fluids, and a hydrocarbon having a general structural formula

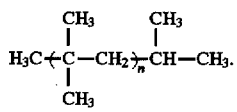

20. The antiperspirant composition of claim 3 wherein the hydrophobic compound is selected from the group consisting of a cyclic volatile siloxane, a linear volatile siloxane, a linear nonvolatile siloxane, a methicone, a phenyltrimethicone, hexyl dimethicone, a polyphenylmethylsiloxane, bisphenylhexamethicone, and mixtures thereof.

21. The antiperspirant composition of claim 1 comprising at least one liquid crystal phase.

22. A gelled or solid antiperspirant composition comprising:

(a) about 5% to about 30% by weight of an aluminum halide, an aluminum hydroxyhalide, a zirconyl oxyhalide, a zirconyl hydroxyhalide, an aluminum zirconium glycinate, or a mixture thereof;

(b) about 0.8% to about 7% by weight of boric acid, sodium tetraborate, or a mixture thereof;

(c) about 1% to about 50% by weight of a nonionic surfactant blend comprising: (i) a first nonionic surfactant having an HLB value of about 10 or greater, and (ii) a second nonionic surfactant having an HLB of less than about 10, wherein a sufficient amount of the first nonionic surfactant is blended with a sufficient amount of the second nonionic surfactant to provide the nonionic surfactant blend having the HLB value of about 10 to about 15; and (d) an aqueous-based carrier, wherein the antiperspirant composition has a pH of about 3 to about 5.

23. The composition of claim 22 further comprising 0% to about 50% by weight of a hydrophobic compound selected from the group consisting of a volatile cyclic siloxane, a volatile linear siloxane, a nonvolatile linear siloxane, isohexadecane, isoeicosane, isopropyl myristate, a polyphenylmethylsiloxane, 1-decene dimer, a mineral oil, a volatile hydrocarbon having a formula

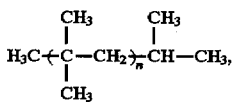

wherein n ranges from 2 to 5, and mixtures thereof.

24. The composition of claim 22 wherein the first surfactant is selected from the group consisting of isoceteth-20, ceteth-20, dimethicone copolyol, an ethoxylated nonylphenol having at least 9 ethylene oxide moieties, an ethoxylated dodecylphenol having at least 9 ethylene oxide moieties, an ethoxylated octylphenol having at least 9 ethylene oxide moieties, steareth-10, PEG-20 glyceryl stearate, steareth-20, POE(6)tridecylether, PEG-80 castor oil, steareth-21, polysorbate 20, an ethoxylated fatty ($C_6$–$C_{22}$) alcohol having at least 9 ethylene oxide moieties, and mixtures thereof.

25. The composition of claim 22 wherein the second surfactant is selected from the group consisting of laureth-4, laureth-3, laureth-2, DEG-8 dioleate, an ethoxylated nonylphenol having less than 9 ethylene oxide moieties, an ethoxylated octylphenol having less than 9 ethylene oxide moieties, an ethoxylated dodecylphenol having less than 9 ethylene oxide moieties, an ethyoxylated fatty ($C_6$–$C_{22}$) alcohol having less than 9 ethylene oxide moieties, and mixtures thereof.

26. A method of treating or preventing malodors associated with human perspiration comprising topically applying an effective amount of an antiperspirant composition to human skin, said composition comprising:

(a) about 1% to about 40% by weight of an antiperspirant compound;

(b) about 0.5% to about 70% by weight of a surfactant selected from the group consisting of a nonionic surfactant or a nonionic surfactant blend, wherein the nonionic surfactant or nonionic surfactant blend has an HLB value of about 3 to about 20; and (d) a carrier comprising water, wherein the antiperspirant composition has a pH of about 3 to about 5, a penetrometer reading of about 4 mm to about 10 mm, and a % transmittance at 700 nm of at least 50%.

27. The method of claim 26 wherein the surfactant comprises a nonionic surfactant or a nonionic surfactant blend, wherein the nonionic surfactant or nonionic surfactant blend has an HLB value of about 10 to about 15.

28. The method of claim 26 wherein the human skin having the antiperspirant composition applied thereon has no visually-observable white residue.

29. A gelled or solid antiperspirant composition comprising:

(a) about 1% to about 40% by weight of an antiperspirant compound;

(b) about 0.5% to about 10% by weight of a borate crosslinker;

(c) about 0.5% to about 70% by weight of a nonionic surfactant blend comprising: (i) a first nonionic surfactant having an HLB value of about 10 or greater, and (ii) a second nonionic surfactant having an HLB of less than about 10, wherein a sufficient amount of the first nonionic surfactant is blended with a sufficient amount of the second nonionic surfactant to provide the nonionic surfactant blend having the HLB value of about 10 to about 15; and (d) a carrier comprising water;

wherein the antiperspirant composition has a pH of about 3 to about 5.

30. A method of treating or preventing malodors associated with human perspiration comprising topically applying an effective amount of an antiperspirant composition to human skin, said composition comprising:

(a) about 1% to about 40% by weight of an antiperspirant compound;

(b) about 0.5% to about 10% by weight of a borate crosslinker;

(c) about 0.5% to about 70% by weight of a nonionic surfactant blend comprising: (i) a first nonionic surfactant having an HLB value of about 10 or greater, and (ii) a second nonionic surfactant having an HLB of less than about 10, wherein a sufficient amount of the first nonionic surfactant is blended with a sufficient amount of the second nonionic surfactant to provide the nonionic surfactant blend having the HLB value of about 10 to about 15; and (d) a carrier comprising water, wherein the antiperspirant composition has a pH of about 3 to about 5.

* * * * *